United States Patent [19]

Astudillo Ley

[11] Patent Number: 5,139,498
[45] Date of Patent: Aug. 18, 1992

[54] DEVICE FOR CLOSING STERNUM IN HEART SURGERY

[76] Inventor: Freddy R. Astudillo Ley, Oskarsvägen 15, S-702 14 Örebro, Sweden

[21] Appl. No.: 678,949
[22] PCT Filed: Oct. 13, 1989
[86] PCT No.: PCT/SE89/00563
§ 371 Date: Apr. 17, 1991
§ 102(e) Date: Apr. 17, 1991
[87] PCT Pub. No.: WO90/04366
PCT Pub. Date: May 3, 1990

[30] Foreign Application Priority Data
Oct. 18, 1988 [SE] Sweden ............... 8803706

[51] Int. Cl.$^5$ .................. A61B 17/56; A61B 17/08
[52] U.S. Cl. ...................................... 606/69; 606/216
[58] Field of Search .............. 606/69, 70, 71, 215, 606/216, 74, 72, 103, 217; 128/69; 411/466, 467, 468, 457, 461; 52/712, 690

[56] References Cited

U.S. PATENT DOCUMENTS

| | | | |
|---|---|---|---|
| 2,383,135 | 8/1945 | Lang | 411/461 |
| 2,780,223 | 2/1957 | Haggland | 606/69 |
| 3,593,709 | 7/1971 | Halloran | 606/69 |
| 4,473,068 | 9/1984 | Oh | 606/69 |
| 4,512,346 | 4/1985 | Lemole | 606/216 |
| 4,583,541 | 4/1986 | Barry | 606/69 |
| 4,905,679 | 3/1990 | Morgan | 606/70 |
| 4,917,704 | 4/1990 | Frey | 128/69 |
| 5,000,166 | 3/1991 | Karpf | 128/69 |
| 5,015,248 | 5/1991 | Burstein | 606/69 |

FOREIGN PATENT DOCUMENTS 1579575 11/1980 United Kingdom .

OTHER PUBLICATIONS

Robicsek et al., "The Prevention and Treatment of Sternum Separation Following Open-Heart Surgery", The Journal of Thoacic and Cardiovascular Surgery, Mar. 26, 1976, pp. 267-268.

Primary Examiner—Michael A. Brown
Attorney, Agent, or Firm—Nixon & Vanderhye

[57] ABSTRACT

A device for closing an opening (12) performed in the sternum during heart surgery and for fixing the breast bone halves (13, 14) in relation to each other is described, said device consisting of (a) a plate (1) comprising two flat, longitudinal, parallel anchoring members (2, 3), which are spaced a distance from each other and provided with through-holes (11), and spaced apart, transverse, flat connection pieces (4, 5, 6) which are connected to the anchoring members to form a rigid unit therewith, and (b) a plurality of attachment wires (15) to be inserted into the breast bone halves from below and into said holes (11), the pairs of end portions of said attachment wires being twisted together to the plate. According to the invention the holes (11) in each anchoring member (2, 3) are disposed in a continuous row from the one end to the other of the anchoring member (2, 3) with a uniform distance between the holes (11) in each row of 2-3 mm, each individual attachment wire (15) being inserted through only one breast bone half (13 or 14) at two positions thereof spaced apart to form a loop (16) which is located in a plane parallel to said opening (12), and each wire end portion of each pair of protruding free wire end portions (17, 18) being arranged to be inserted through that hole in the row of holes (11) which is located opposite or nearly opposite the wire end portion (17 or 18).

20 Claims, 2 Drawing Sheets

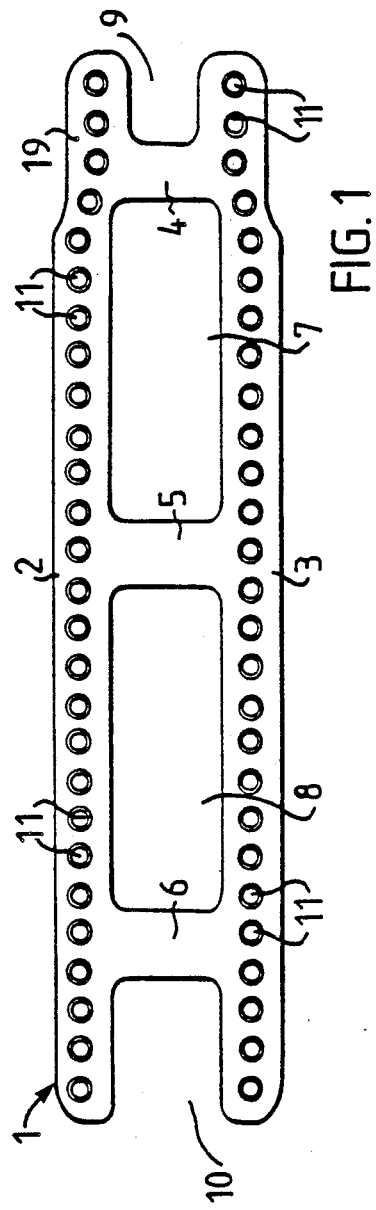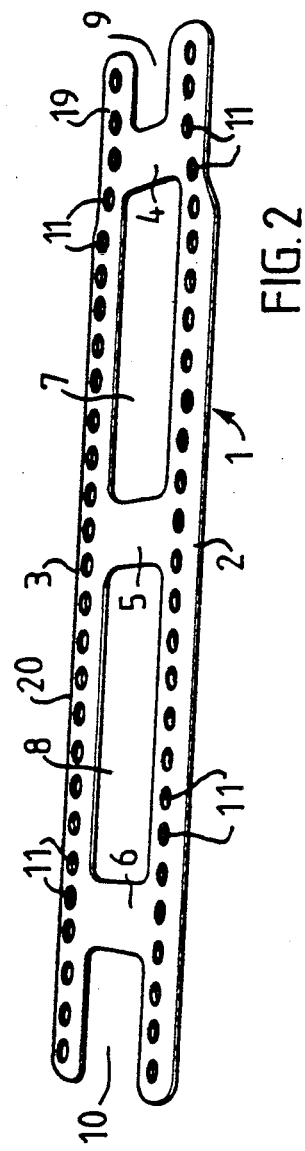

DEVICE FOR CLOSING STERNUM IN HEART SURGERY

The present invention relates to a device for closing an opening performed in the sternum during heart surgery and for fixing the two breast bone halves separated by said opening, in relation to each other, said device consisting of (a) an elongate plate comprising two flat, thin, longitudinal, parallel, uniform anchoring members, which are spaced a predetermined distance from each other and provided with through-holes, and at least two spaced apart, transverse, flat, thin connection pieces which are connected to the anchoring members to form a rigid unit therewith, and (b) a plurality of attachment wires to be inserted into the breast bone halves from below and into said holes, the pairs of end portions of said attachment wires being twisted together to the plate.

Wires, applied in various ways, are used to close the long opening made in the sternum, i.e. the breast bone, during heart surgery and to fix the two breast bone halves together (see The Journal of Thoracic and Cardiovascular Surgery, 1977-78, pages 267-268). One technique is to drill a number of through-holes in the two breast bone halves and thread lengths of wire through the holes so that the lengths of wire extend across the opening, subsequently twisting the ends of each wire together. Another technique is to entirely surround the two breast bone halves with lengths of wire and twist the ends together in order, in the same way, to form a transversal wire joint which draws the breast bone halves towards each other, thus closing the opening and fixing the breast bone halves together. However, in certain cases the wire may cut through the breast bone halves, destroying the wire joint and causing the breast bone to crack along the previous opening. This risk is particularly great if the quality of the breast bone is poor or the patient suffers from a chronic obstructive pulmonary disease, or a combination of these conditions. Sternum insufficiency, i.e. when the breast bone cracks, resulting in open wounds, constitutes one of the most serious and difficult post-operative complications, particularly if an infection occurs as happens in most cases. For patients who have undergone heart surgery, this complication in many cases entails several extra months in hospital and usually a plurality of unsuccessful operations attempting to join the thorax. It is also known through U.S. Pat. No. 4,512,346 and U.S. Pat. No. 4,583,541 to combine the attachment wires with different types of means, however, also in these cases the attachment wires are passed through the two breast bone halves and are attached across the opening. Consequently, the above problem persists. Through GB 1 579 575 it is known to use a bone plate having two anchoring members which are connected by inclined cross pieces and having a few holes. This bone plate is intended to be attached in opposite bone sections of a bone fracture by means of screws inserted in said holes, i.e. the longitudinal direction of the bone plate is substantially perpendicular to the fracture opening or surfaces. However, such a bone plate is not useful for fixing the breast bone halves to each other. Neither the specification gives any suggestions or proposals for solving the problem associated with the closure of sternum in connection with heart surgery. In this context it would also be noted that the behaviour of sternum in the healing process subsequent to median sternotomi does not in any way follow the same rules as those for other bones in the body. This is because sternum is in direct connection with the function of breathing. The treatment of sternum and its complications constitutes therefore a specific problem.

The object of the present invention is to greatly reduce the problems mentioned above and to provide a device which, in an efficient and simple manner, can be used to close and fix the breast bone after opening for heart surgery.

The novelty of the invention resides in that the holes in each anchoring member are disposed in a continuous row from the one end to the other of the anchoring member with a uniform distance between the holes in each row of 2-3 mm, each individual attachment wire being inserted through only one breast bone half at two positions thereof spaced apart to form a loop which is located in a plane substantially parallel to said opening, and each wire end portion of each pair of protruding free wire end portions of an attachment wire being arranged to be inserted through that hole in the row of holes which is located opposite or nearly opposite the wire end portion.

The invention will be described further in the following with reference to the drawings in which FIG. 1 is a view from above of a plate of the device according to the invention, and FIG. 2 is a perspective view of the plate according to FIG. 1 seen from the opposite side.

Figure 3:
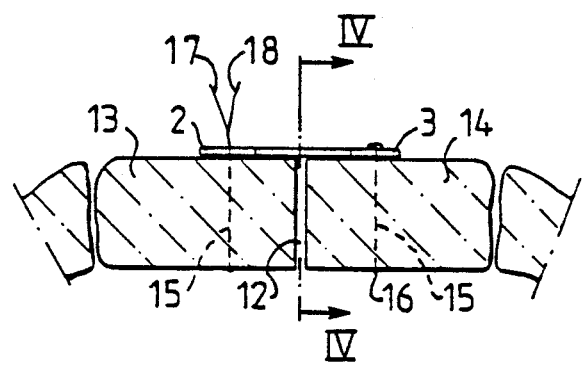
FIG. 3 is a cross section of sternum and the plate according to FIG. 1 and shows attachment wires inserted through the breast bone halves.
Figure 4:
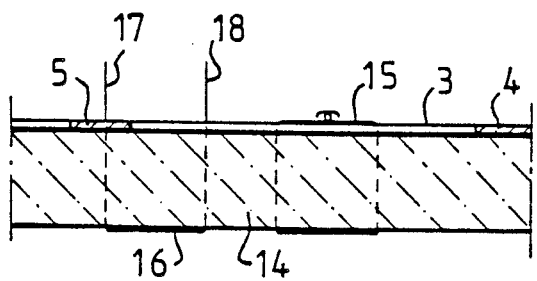
FIG. 4 is a longitudinal section of one of the breast bone halves and the applied device according to the invention.

The device shown in the drawings comprises an elongate plate 1, substantially rectangular in shape and having two longitudinal, flat, thin, parallel, uniform anchoring members 2, 3 spaced a predetermined distance from each other, and three transverse flat, thin, parallel connection pieces 4, 5, 6 extending between the anchoring members 2, 3 and being connected thereto to form a rigid unit. Thus, the plate is manufactured in one piece, the anchoring members extending along its longitudinal sides. The two outer connection pieces 4, 6 are located a suitable distance from the ends of the plate 1 and at substantially the same distance from the central connection piece 5. The connection pieces 4, 5, 6 are sufficiently wide and strong so that the plate is stable and the anchoring members 2, 3 are spaced from each other even when the plate is subjected to stress. Openings 7, 8 are formed between the connection pieces 4, 5, 6 and notches 9, 10 are formed outside the two outer connection pieces 4, 6. The plate is thus lighter and less material is required. At the one end the plate 1 has a short, somewhat narrower part 19 than its other main part 20, thus giving the anchoring members 2, 3 a curved or indented shape suited to the shape of the upper section of the sternum. In this short end part 19 the anchoring members 2, 3 are still parallel to each other.

Further, each anchoring member 2, 3 is provided with a plurality of small through-holes 11, located in a row close together and thus extending from one flat side of the plate to its other flat side, i.e. through the thickness direction of the anchoring members 2, 3. According to the present invention, the holes 11 in each anchoring member is arranged in a continuous row from one end to the other of the anchoring member and spaced from each other a uniform distance of 2-3 mm. The holes 11 have suitably a diameter of about 1.0-1.5 mm.

Further, the device includes a plurality of attachment wires 15 to be inserted from below into the two breast bone halves 13, 14 which are separated by an opening performed in the sternum.

Depending on the size of the sternum, the plate is about 135-155 mm long, preferably 140-145 mm, and is about 30-45 mm wide, preferably about 35 mm. The plate is about 0.3-1.0 mm thick, preferably 0.5-0.7 mm. The anchoring strips have a uniform width of 6-10 millimeters, preferably 8 millimeters. The width at the first end of the plate is 4-8 millimeters less than the width along the rest of the plate. The holes are bevelled on at least one side of the plate, i.e. the side which is to face out, in order to prevent damage to the attachment wire used to secure sternum to the plate 1.

The plate is suitably manufactured of metal, e.g. stainless steel. With the preferred dimensions it then weighs about 12 g. The plate is preferably deformable in order to facilitate and ensure accurate implanting above the breast bone.

Before applying the plate, a plurality of holes are made after each other by means of a suitable tool in the breast bone halves at a predetermined distance from the incision surfaces of the opening 12. Determined lengths of attachment wires are then threaded through the last-mentioned holes from below so that the two end portions 17, 18 of an attachment wire extend through and out from two holes in one and the same breast bone half 13 or 14. Said two holes in the breast bone half 13 or 14 are located at a suitable distance from each other so that the attachment wire 15 forms a loop 16 which exists after twisting the attachment wire against the plate, i.e. the holes in the breast bone halves 13 or 14 must not be so near each other that bone or tissue parts located therebetween are weakened and penetrated by the loop 16 of the attachment wire. The plate is moved down to the breast bone with its underside facing thereto so that each anchoring member 2, 3 will cover only one of the breast bone halves 13, 14 with the opening 12 located between the anchoring members 2, 3. In the practice the opening 12 is smaller than shown in FIG. 3. During this lowering of the plate each wire end portion of each pair of wire end portions 17, 18 is guided in to and through that hole 11 in the row of holes which is located closest to the wire end portion 17 or 18 and which may be considered to be a substantially opposite hole. Each pair of wire end portions 17, 18 can then be twisted together tight to the anchoring member 2 or 3. The large number of holes 11 in each anchoring member 2, 3 facilitates orientation and insertion of the wires ends 17, 18, ensuring that a hole 11 is always to be found opposite or nearly opposite a wire end portion directed straight upward which thus easily can be passed through said hole, and also ensuring that the sections of the wire end portions located close under the plate in the breast bone are not pulled in direction to each other any appreciable way into the breast bone since the distance between the two holes for the wire end portions has been able to be selected so that it corresponds to or nearly corresponds to the width of the loop 16. The anchoring member 2, 3 will effectively relieve strain on the breast bone halves so that the attachment wires 15 do not cut into them. The tension forces of the attachment wires will be exerted uniformly on the bone in the extension of the attachment wire therethrough. The loop 16 of the attachment wire is furthermore located advantageously in a plane parallel to and spaced from the incision surfaces of the opening 12 and not perpendicular thereto as in the case of the techniques using transversal attachment wires, described in the introduction. By disposing the attachment wires 15 parallel to the opening 12 and not across this the sternum receives a greater fixing surface against the plate 1, this being essential since sternum is the weakest link of the joint. As will be seen in FIG. 3 the plate 1 and the attachment wires 15, seen in a cross section through the breast bone halves 13, 14 and opening 12, a U-shaped joint and not a circular or oval joint as is the case in the known devices. The forces acting onto the breast bone halves, when, for instance, the patient gets a cough, will be absorbed by the plate and uniformly distributed to the attachment wires 15 at an essentially reduced risk of cutting the attachment wires into the breast bone halves in the direction to the closed opening 12 which thus will be kept closed so that the breast bone halves are permitted to grow together in a desirable manner.

The attachment wires may consist of a suitable metal material such as stainless steel or a titanium alloy.

The device according to the invention can be advantageously used as a prophylactic measure in the treatment of sternum insufficiency. It can thus be used as a prophylactic measure on patients suffering from severe pulmonary diseases or obesity, or whose sternum is in poor condition, and for patients where the sternum has not been opened by a central incision line.

I claim:

1. A device for closing an elongated opening in a severed sternum, for fixing the sternum portions on either side of the opening together, comprising:
    an elongated plate comprising first and second flat, thin, longitudinal, parallel, uniform anchoring strips which are held together in parallel relationship and are spaced from each other a predetermined distance;
    means defining a plurality of through-extending holes formed in said anchoring strips, said holes disposed in continuous rows from one end to the other of each of said elongated strip, with a uniform distance between the holes in each row of about 2-3 millimeters; and
    wherein said anchoring strips are held parallel to each other by a plurality of parallel spaced apart, transverse, flat connecting elements, which are connected to said anchoring strips to form said plate as a rigid unit.

2. A device as recited in claim 1 wherein said elongated plate has first and second ends, and wherein said anchoring strips at said first end are spaced closer to each other, to accommodate the upper section of the sternum, than are the anchoring strips at said second end.

3. A device as recited in claim 2 wherein said anchoring strips each have a uniform width of about 6-10 millimeters, and wherein said plate has a uniform width over the majority of the length thereof of about 30-45 millimeters, and a width at said first end thereof of about 4-8 millimeters less than the width along the rest of the plate.

4. A device as recited in claim 3 wherein said anchoring strips have a width of about 8 millimeters, and wherein said elongated plate has a width, over the majority of the length thereof, of about 35 millimeters.

5. A device as recited in claim 3 wherein said plurality of transverse connection pieces comprises three transverse connecting pieces evenly spaced along said plate in the dimension of elongation thereof.

6. A device as recited in claim 1 wherein said anchoring strips each have a uniform width of about 6–10 millimeters, and wherein said plate has a uniform width over the majority of the length thereof of about 30–45 millimeters.

7. A device as recited in claim 6 wherein said anchoring strips have a width of about 8 millimeters, and wherein said elongated plate has a width, over the majority of the length thereof, of about 35 millimeters.

8. A device as recited in claim 6 wherein said plurality of transverse connection pieces comprises three transverse connecting pieces evenly spaced along said plate in the dimension of elongation of said anchoring strips.

9. A device as recited in claim 6 in combination with a plurality of attachment wires, a first attachment wire extending between a pair of holes in said first anchoring strip to form a first loop which is located in a plane substantially parallel to the dimension of elongation of said anchoring strips, the opening in the sternum, and a second wire loop in said second anchoring strip, associated with said second strip holes in alignment with said first strip holes receiving said first loop.

10. A device as recited in claim 9 wherein each of said holes has a diameter of about 1.0–1.5 millimeters, and they are beveled in order to prevent damage to the attachment wires.

11. A device as recited in claim 10 wherein said plate is about 0.3–1.0 millimeters thick, and is stainless steel; and wherein said attachment wires are selected from the group consisting essentially of stainless steel and titanium alloys.

12. A device as recited in claim 5 wherein said plurality of transverse connection pieces comprises three transverse connecting pieces evenly spaced along said plate in the dimension of elongation thereof.

13. A device as recited in claim 5 in combination with a plurality of attachment wires, a first attachment wire extending between a pair of holes in said first anchoring strip to form a first loop which is located in a plane substantially parallel to the dimension of elongation of said anchoring strip, the opening in the sternum, and a second wire loop in said second anchoring strip, associated with said second strip holes in alignment with said first strip holes receiving said first loop.

14. A device as recited in claim 13 wherein each of said holes has a diameter of about 1.0–1.5 millimeters, and they are beveled in order to prevent damage to the attachment wires.

15. A device as recited in claim 14 wherein said plate is about 0.3–1.0 millimeters thick, and is stainless steel; and wherein said attachment wires are selected from the group consisting essentially of stainless steel and titanium alloys.

16. A method for closing a severed sternum, having first and second portions separated by an elongated opening, utilizing an elongated plate having first and second flat, thin, longitudinal, parallel, uniform anchoring strips which are spaced a predetermined distance from each other and held rigidly in parallel position by a plurality of spaced transverse flat, thin, connecting pieces, the anchoring strips having a plurality of aligned uniformly spaced holes formed therein and in substantial alignment with corresponding holes on the other anchoring strip, said uniform distance between said holes in each row is 2–3 millimeters; said method comprising the steps of substantially sequentially:
 (a) placing the first anchoring strip in operative association with the first portion of the sternum;
 (b) inserting a wire through a pair of holes in the first anchoring strip and closing the free ends of the wires so that a first closed loop of wire is formed which extends generally parallel to the dimension of elongation of the first anchoring strip and the opening in the sternum;
 (c) placing the second attaching strip into contact with the second portion of the sternum; and
 (d) repeating step (b) for holes in the second anchoring strip, the holes in the second anchoring strip through which the wire extends being substantially in alignment with the holes in the first anchoring strip through which the first closed wire loop extends.

17. A method as recited in claim 16 comprising the further step (b1), prior to step (c), of disposing a wire in association with the second sternum portion so that the free ends of the wire pass through the sternum second portion and are spaced from each other in a dimension parallel to the opening in the sternum; and wherein steps (c) and (d) are practiced by initially lowering the plate second anchoring strip into contact with the sternum so that the free ends of the wires pass through holes in the second strip substantially aligned with the wire receiving openings in the first strip.

18. A method as recited in claim 17 wherein the anchoring strips of the plate have a first end at which they are located closer together than over the rest of the length of the strips; and wherein said method is practiced by orienting the plate so that the first end of the plate is at the top of the sternum, where the sternum is narrower.

19. A method as recited in claim 16 wherein steps (b) and (d) are repeated at a number of places along each portion of the sternum.

20. A method of prophylactically treating a patient suffering from severe pulmonary diseases or obesity, or whose sternum is in poor condition, utilizing an elongated plate having first and second flat, thin, longitudinal, parallel, uniform anchoring strips which are spaced a predetermined distance from each other and held rigidly in parallel position by a plurality of parallel spaced transverse flat, thin, connecting pieces, each anchoring strip having a plurality of aligned uniformly spaced holes formed therein and in substantial alignment with corresponding holes in the other anchoring strip; said method comprising the steps of:
 (a) placing the first anchoring strip so that it is on one side of the vertical center line through the sternum;
 (b) inserting a wire through a pair of holes in the first anchoring strip and closing the free ends of the wires so that a closed loop of wire is formed which extends generally parallel to the vertical center line of the sternum;
 (c) bringing the second anchoring strip of the plate into contact with the sternum on the opposite side of the center line of the sternum from the first anchoring strip; and
 (d) repeating step (b) for holes in the second anchoring strip, the holes in the second anchoring strip through which the wire extends being substantially in alignment with the holes in the first anchoring strip through which the wire extends.

* * * * *